(12) United States Patent
Chornenky et al.

(10) Patent No.: US 8,906,006 B2
(45) Date of Patent: *Dec. 9, 2014

(54) METHOD OF DESTROYING TISSUE CELLS BY ELECTROPORATION

(71) Applicant: AngioDynamics, Inc., Latham, NY (US)

(72) Inventors: Victor Chornenky, Minnetonka, MN (US); Ali Jaafar, Eden Prairie, MN (US)

(73) Assignee: AngioDynamics, Inc., Latham, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/176,889

(22) Filed: Feb. 10, 2014

(65) Prior Publication Data

US 2014/0155977 A1   Jun. 5, 2014

Related U.S. Application Data

(63) Continuation of application No. 13/556,455, filed on Jul. 24, 2012, now Pat. No. 8,647,338, which is a continuation of application No. 12/501,225, filed on Jul. 10, 2009, now Pat. No. 8,251,986, which is a continuation of application No. 11/106,835, filed on Apr. 15, 2005, now Pat. No. 7,938,824, which is a continuation of application No. 09/931,672, filed on Aug. 17, 2001, now Pat. No. 6,892,099.

(60) Provisional application No. 60/267,106, filed on Feb. 8, 2001, provisional application No. 60/225,775, filed on Aug. 17, 2000.

(51) Int. Cl.
  *A61B 18/14* (2006.01)
  *C12N 13/00* (2006.01)
  *A61N 1/04* (2006.01)
  *A61B 18/00* (2006.01)

(52) U.S. Cl.
  CPC .............. *A61N 1/0412* (2013.01); *A61B 18/14* (2013.01); *A61B 18/1445* (2013.01); *A61B 18/1477* (2013.01); *A61B 2018/00452* (2013.01); *A61B 2018/00613* (2013.01); *A61B 2018/1425* (2013.01); *A61B 2018/143* (2013.01)
  USPC .................. 606/32; 606/41; 607/2; 607/115; 435/173.6

(58) Field of Classification Search
  CPC ........ A61B 18/04; A61B 18/12; A61B 18/14; A61B 18/18; A61B 18/1442; A61B 18/1445; A61B 18/1477; A61B 18/1482; A61B 2018/00613
  USPC ................ 606/27–42; 607/2, 3, 72, 101–102, 607/115–116; 604/20–22; 435/173.6, 435/285.2, 461
  See application file for complete search history.

(56) References Cited

U.S. PATENT DOCUMENTS 5,944,710 A * 8/1999 Dev et al. ........................ 604/500
5,968,006 A * 10/1999 Hofmann ........................ 604/20

(Continued)

*Primary Examiner* — Michael Peffley
*Assistant Examiner* — Khadijeh Vahdat
(74) *Attorney, Agent, or Firm* — Ryan D. Artis

(57) ABSTRACT

An apparatus and method for performing non-invasive treatment of the human face and body by electroporation in lieu of cosmetic surgery is provided. The apparatus comprises a high voltage pulse generator and an applicator having two or more electrodes in close mechanical and electrical contact with the patient's skin for applying the pulses to the patient's skin. The applicator may consist of two pieces with one electrode having a sharp tip and another having a flat surface. High voltage pulses delivered to the electrodes create at the tip of the sharp electrode an electric field high enough to cause death of relatively large subcutaneous fat cells by electroporation. Moving the electrode tip along the skin creates a line of necrotic subcutaneous fat cells, which later are metabolized by the body. Multiple applications of the electrode along predetermined lines on the face or neck create shrinkage of the skin and the subcutaneous fat volume underlying the treated area.

10 Claims, 6 Drawing Sheets

(56) References Cited

U.S. PATENT DOCUMENTS

| | | | |
|---|---|---|---|
| 6,326,177 B1 * | 12/2001 | Schoenbach et al. | 435/173.7 |
| 6,387,671 B1 * | 5/2002 | Rubinsky et al. | 435/173.7 |
| 6,892,099 B2 * | 5/2005 | Jaafar et al. | 607/72 |
| 6,962,587 B2 * | 11/2005 | Johnson et al. | 606/41 |
| 7,938,824 B2 * | 5/2011 | Chornenky et al. | 606/32 |
| 8,251,986 B2 * | 8/2012 | Chornenky et al. | 606/32 |
| 8,647,338 B2 * | 2/2014 | Chornenky et al. | 606/32 |
| 2001/0044596 A1 * | 11/2001 | Jaafar | 604/103.01 |
| 2002/0040204 A1 * | 4/2002 | Dev et al. | 604/20 |

* cited by examiner

METHOD OF DESTROYING TISSUE CELLS BY ELECTROPORATION

CROSS-REFERENCE TO RELATED APPLICATIONS

This is a continuation of U.S. application Ser. No. 13/556,455, filed Jul. 24, 2012, now U.S. Pat. No. 8,647,338, which is a continuation of U.S. application Ser. No. 12/1501,225, filed Jul. 10, 2009, now U.S. Pat. No. 8,251,986, which is a continuation of U.S. application Ser. No. 11/106,835, now U.S. Pat. No. 7,938,824, filed Apr. 15, 2005, which is a continuation of U.S. application Ser. No. 09/931,672, filed Aug. 17, 2001, now U.S. Pat. No. 6,892,099, which claims priority to U.S. provisional application Ser. No. 60/267,106, filed Feb. 8, 2001 and to U.S. provisional application Ser. No. 60/225,775, filed Aug. 17, 2000, all of which are incorporated herein by reference.

FIELD OF THE INVENTION

The present invention relates generally to electroporation of tissues and, specifically, to apparatus and methods for reducing subcutaneous fat deposits, performing virtual face lifts, and body sculpturing.

BACKGROUND OF THE INVENTION

"Cosmetic surgery" is a phrase used to describe broadly surgical changes made to a human body with the usual, though not always, justification of enhancing appearance. This area of medical practice constitutes an ever-growing industry around the world. Obviously, where such a procedure fails to deliver an enhanced appearance, the procedure fails to meet the desired goal. One of the reasons that the majority of current procedures fail to deliver upon their promise is that, for the most part, current procedures are invasive, requiring incisions and suturing, and can have serious and unpleasant side effects, including but not limited to scarring, infection, and loss of sensation.

One of the more common forms of cosmetic surgery is the "face-lift." A face-lift is intended to enhance facial appearance by removing excess facial skin and tightening the remaining skin, thus removing wrinkles. A face-lift is traditionally performed by cutting and removing portions of the skin and underlying tissues on the face and neck. Two incisions are made around the ears and the skin on the face and neck is separated from the subcutaneous tissues. The skin is stretched, excess tissue and skin are removed by cutting with a scissors or scalpel, and the skin is pulled back and sutured around the ears. The tissue tightening occurs after healing of the incisions because less skin covers the same area of the face and neck and also because of the scars formed on the injured areas are contracting during the healing process.

Traditional face-lift procedures are not without potential drawbacks and side effects. One drawback of traditional cosmetic surgery is related to the use of scalpel and scissors. The use of these devices sometimes leads to significant bleeding, nerve damage, possible infection and/or lack of blood supply to some areas on the skin after operation. Discoloration of the skin, alopecia (boldness), is another possible side effect of the standard cosmetic surgery. The overall quality of the results of the surgery is also sometimes disappointing to the patients because of possible over-corrections, leading to undesired changes in the facial expression. Additionally, face-lift procedures require a long recovery period before swelling and bruising subside.

The use of lasers to improve the appearance of the skin has been also developed. Traditional laser resurfacing involves application of laser radiation to the external layer of the skin—the epidermis. Destruction of the epidermis leads to rejuvenation of the epidermis layer. The drawback of the laser resurfacing procedure is possible discoloration of the skin (red face) that can be permanent.

Another laser procedure involves using optical fibers for irradiation of the subcutaneous tissues, such as disclosed in U.S. Pat. No. Re36,903. This procedure is invasive and requires multiple surgical incisions for introduction of the optical fibers under the skin. The fibers deliver pulsed optical radiation that destroys the subcutaneous tissues as the tip of the fiber moves along predetermined lines on the face or neck. Debulking the subcutaneous fat and limited injury to the dermis along the multiple lines of the laser treatment results in contraction of the skin during the healing process, ultimately providing the face lift. The drawback of the method is its high price and possibility of infection.

Electrosurgical devices and methods utilizing high frequency electrical energy to treat a patient's skin, including resurfacing procedures and removal of pigmentation, scars, tattoos and hairs have been developed lately, such as disclosed in U.S. Pat. No. 6,264,652. The principle drawback of this technology is collateral damage to the surrounding and underlying tissues, which can lead to forming scars and skin discoloration.

Other forms of cosmetic surgery are also known. One example is liposuction, which is an invasive procedure that involves inserting a suction device under the skin and removing fat tissues. As with other invasive surgical procedures, there is always a risk of infection. In addition, because of the invasive nature of the procedure, physicians usually try to minimize the number of times the procedure must be performed and thus will remove as much fat tissue as possible during each procedure. Unfortunately, this procedure has resulted in patient deaths when too much tissue was removed. Assuming successful removal of excess fat tissue, further invasive surgery may be required to accomplish desired skin tightening.

The prior art to date, then, does not meet the desired goal of performing cosmetic surgery in a non-invasive manner while causing minimal or no scarring of the exterior surface of the skin and at the same time resulting in the skin tightening.

Objects of the Invention

It is an object of the present invention to provide an apparatus and method which uses electroporation to cause necrosis of cells in the subcutaneous layer of fat and the interior side of the dermis, resulting in the contraction and tightening of the skin. In particular, it is an object of the present invention to provide method and apparatus for performing face and neck lift and others similar procedures on the face in a non-invasive manner.

Another object of the present invention is to provide an apparatus and method for significant bulk reduction of the number of subcutaneous fat cells in the body, resulting in a significant weight loss.

Still another object of the present invention is to provide non-invasive apparatus and method for cosmetic and weight loss procedures.

Still another object of the invention is to provide an apparatus and method for selective removal of fat in different areas to enable changing the shape of the body, or body sculpturing.

SUMMARY OF THE DISCLOSURE

The present invention provides an apparatus and method for creation of a controlled injury or alteration to the subcutaneous tissue and/or underside of the dermis, with the following healing process leading to the contraction of the skin; and/or to the controlled destruction of fat cells, leading to their permanent loss. In the present invention the damage to the subcutaneous tissue, underside of the dermis, and/or fat cells is caused by electroporation.

An apparatus in accord with the current invention comprises a voltage pulse generator, an applicator with two or multiple electrodes of different shapes and sizes and a cable connecting the electrodes to the pulse generator. The pulse generator produces set of high voltage pulses of predetermined amplitude, duration and number to cause necrosis in a treated area of subcutaneous tissues.

A method in accord with the current invention comprises application of electrical pulses to the electrodes positioned on the skin in a treatment area. For a face lift, flat and needle-like electrodes are used, the last one providing a strong and non-uniform electric field predominantly normal to the surface of the skin. The amplitude, duration and number of applied pulses are selected to cause necrosis of fat cells to a predetermined depth in the subcutaneous tissue and a limited necrosis of the underside of the dermis. A number of lines of predetermined pattern are exposed to electroporation. Later, during the healing process the skin on the treated area contracts. The injury to the tissues made by electroporation is very gentle and selective; it does not produce scars on the epidermis, the most external layer of the skin.

A method of weight loss and body sculpturing in accord with the present invention comprises application of electroporation pulses to a significant volume of fat tissue. In this case both electrodes are flat and attached to the arms of a forceps. The electrodes are moveable towards and away from each other and are capable of pinching skin with underlying subcutaneous fat and electroporating it. Application of flat, parallel electrodes produces a electric field is uniform in the tissue that effects only fat cells.

For weight loss a voltage generator coupled to multiple needle type electrodes may be used.

In another embodiment of the present invention, an electroporation apparatus for bulk weight loss may comprise apparatus for production of a pulsed magnetic field and its application to the area to be treated. In this embodiment of the present invention, a curl electric field for the electroporation of subcutaneous fat is created by the pulsed magnetic field. Curl electric field causes eddy currents in the tissue and at an appropriate amplitude above kills the fat cells.

BRIEF DESCRIPTION OF THE DRAWINGS

The objects and advantages of the present invention will be appreciated from the following specification when read in conjunction with the accompanying drawings wherein:

FIG. 3 is a schematic illustration of different applicators of the present apparatus wherein

DESCRIPTION OF THE PREFERRED EMBODIMENTS

Figure 1:
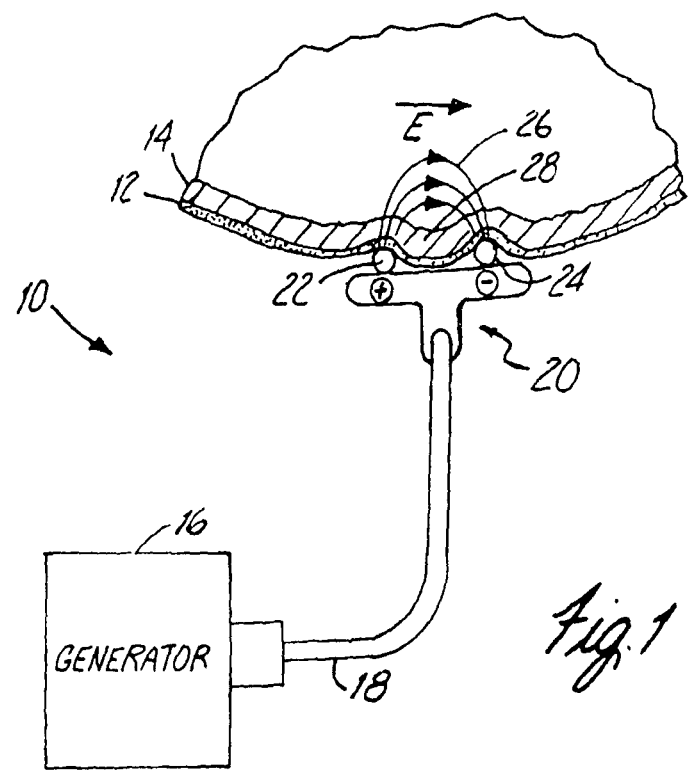
FIG. 1 is a schematic illustration of an apparatus with an applicator having an array of symmetric electrodes shown during electroporation treatment.

The term "electroporation" (EP) refers to the use of electric field pulses to induce microscopic pores in the cell membranes called "electropores". Depending on the parameters of the electric pulse, an electroporated cell can survive the pulse or die. The cause of death of an electroporated cell is believed to be a chemical imbalance, resulting from the fluid communication with the extra cellular environment through the pores. The number and size of electropores created depends on the product of the amplitude E and duration t of the pulse. Below a certain limit, no electropores are induced at all. This limit is different for different cells and depends, principally, on their sizes. The smaller the cell, the higher the product of the amplitude and duration must be to induce pores. Above the lower limit the number of pores and their effective diameter increases with the product Et. Until an upper limit is achieved, cells survive pulsing and restore their viability thereafter. Above the upper limit the pores diameters and number become too large for a cell to survive. It cannot repair itself by any spontaneous or biological process and dies. As noted, a cell's vulnerability to an electric field depends on its size: the larger the cell, the lower the electric field required for killing it. If cells of different sizes are exposed to the same electric field, the largest cells are the first to die. Thus, application of an electric field having preselected parameters can result in selectively killing particular cells.

A desirable target for cell death using the present invention is adipose tissue, commonly called fat. Adipose cells do not proliferate in adults. Their number is fixed at a very early age. Adipose cells can change their size by accumulating or loosing lipids and be responsible for significant, up to two-fold increase in the body weight. Cutting down in the number of large adipose cells results in a significant weight loss in the fat tissue and the whole body. If fat cells are destroyed by any means, their content is metabolized by the body, i.e., scavenged by macrophages, and their number is not restored. The loss of adipose cells, then, is permanent.

Adipose tissue consists of lipid-filled cells ranging in size from 25 to 200 microns. An applied electric field affects the various sized cells differently as previously mentioned. For example, if an electric field, equal to the upper electroporation limit for 100 micron cells (about 10-20 V/mm) is applied to a fat tissue, all cells with sizes from 100 micron and above, will die. The dead cells will be disposed later by macrophages, and the body will metabolize the lipids stored in these cells. Small adipose cells, for which the applied electric field is below the upper electroporation limit, survive any number of electric pulses without any morphological or functional damage.

Pulsed electric fields can be applied to fat deposits inside the body by different methods. In a first method two electrodes are applied to the skin over the fat tissue at some distance from each other and electric microsecond pulses are applied by the electrodes to the tissue. The pulse electric field, created by these two electrodes is non-uniform; it is higher near the electrodes and decreases with the depth. The electric field at the fat deposits should reach several tens of volts per mm to be able to kill adipose cells of large diameters. At the skin level the non-uniform electric field will be significantly higher. To be harmless for the skin cells, the field should not exceed the value of the upper electroporation limit for skin cells. The cells in the epidermic basal layer of the skin, which is responsible for the mitotic division and continuous rejuvenation of the skin, have dimensions of about 10 microns or less (6-10 microns). This is 10 or more times less than that of the targeted adipose cells, which is about 100 microns and larger as noted earlier. The upper electroporation limit for the skin cells in accordance with their size is therefore about 10 times higher than that of adipose cells of 100 microns diameter.

A second method of applying an electric field to the subcutaneous adipose tissue or the skin is by applying short magnetic pulses preferentially normally to the skin. The transient magnetic field creates curl electric field in the skin and the underlying tissues. This curl electric field causes eddy currents in the cells. If the magnitude of this transient electric field reaches the upper electroporation limit for the cells, it will kill them exactly as does the potential electric field created by charged electrodes.

The depth of penetration of the electric field in the skin and the fat tissue under it depends on the distance between the electrodes, their shape and size. The larger the size of electrodes and the distance between them, the deeper the penetration will be. If the electrodes are small enough and the distance between them is short, the electric field penetrates only into the skin and does not reach the underlying tissues.

If pulsed electric field penetrates only in the skin and its amplitude is high enough to kill skin cells (several hundred volts per mm), electroporation can be used for selective cell killing. The dead cells are removed by macrophages and the skin shrinks during the healing process. This skin shrinkage can be planned in advance both in terms of directions and degree. By selecting a number, direction and length of the electroporation "cuts" the operator can control the future shrinks. This method can be used for correcting wrinkles and skin pouches on the face, the neck, and on the upper and lower eye lids.

The skin electroporation treatment together with fat reducing electroporation treatment can be used as alternative to cosmetic surgery for the face lift, the upper and lower eye lid surgery, the forehead lift and body sculpturing practically in all parts of the human body.

An electroporation treatment presents several notable advantages over present cosmetic surgery procedures. First, an electroporation treatment is sterile. The most upper layer of the skin, comprising horny dead cells, is very resistant to any damage from an electroporation treatment; it protects the lower layers of the skin from infection.

The electroporation virtual facelift and body sculpturing can be performed in step by step fashion in a multi-session process. This method allows taking into account actual results of previous sessions and directs process of reshaping of the face or body to desired objectives. The treatment can be performed by a medical professional or by the patient him/herself.

With the foregoing generalized explanation of the present invention, apparatus in accord therewith may be described. Referring to FIG. 1, an electroporation system 10 in accord with the invention is schematically shown with a cross section of a piece of skin 12 with subcutaneous tissue 14 during electroporation treatment. Electroporation system 10 includes a power supply 16 for generating high voltage pulses that are sent though an appropriate electrical connector 18 to an applicator 20. Applicator 20 includes electrodes 22 and 24 that engage skin 12 and will be appropriately insulated to ensure safe handling. Additionally, the applicator will preferably be configured so as to ensure ease of handling, and thus could take many forms. The electrodes 22 and 24 may take the form of needle electrodes. The electric field created between the electrodes 22 and 24 is depicted with field lines 26 and is applied to the skin 12 and subcutaneous tissue or fat 14. In the areas close to the electrodes the electric field has an amplitude exceeding the upper electroporation limit, thus causing death to fat cells. This area of fat cell necrosis is indicated at 28.

Figure 2:
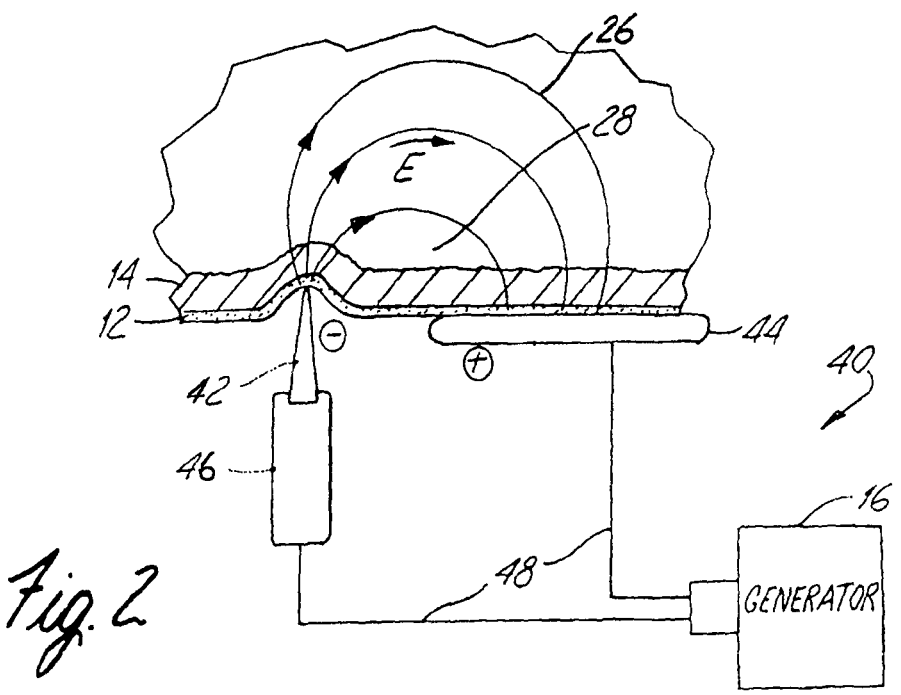
FIG. 2 is a schematic illustration of an apparatus with an applicator having one flat electrode and one a needle like electrode shown during electroporation treatment.

In FIG. 2 an alternative embodiment 40 of the present invention is shown with an applicator having two members: a needle-like electrode 42 and a flat electrode 44. If desired, the system 40 may include an insulating handle 46 configured to be held by an operator to facilitate the manual manipulation of the electrode 42. The high voltage pulse power supply 16 is connected to the applicator electrodes 42 and 44 by appropriate electrical connectors 48. Both electrodes 42 and 44 are engaged with skin 12. Electric field lines 26 depict an electric field between the electrodes 42 and 44. The area 28, where the electric field is the highest, is the treatment area where the amplitude of the electric field exceeds the upper electroporation limit and causes cell death.

Figure 3C:
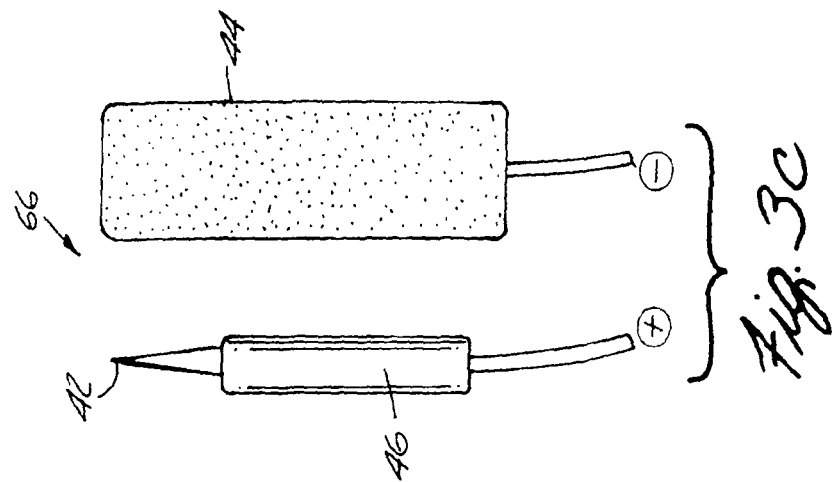
FIG. 3c illustrates applicator having one flat electrode and one needle like electrode.
Figure 3B:
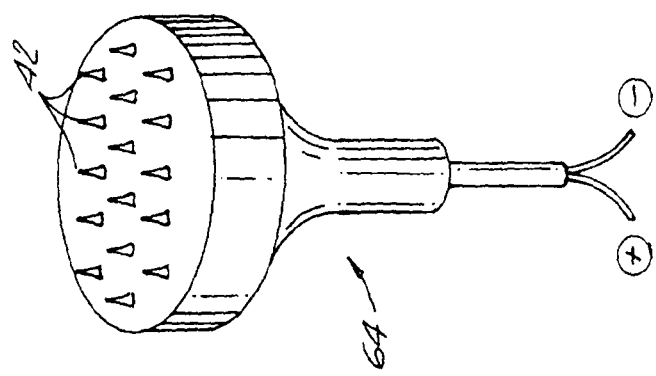
FIG. 3b illustrates an applicator having an array of needle like electrodes.
Figure 3A:
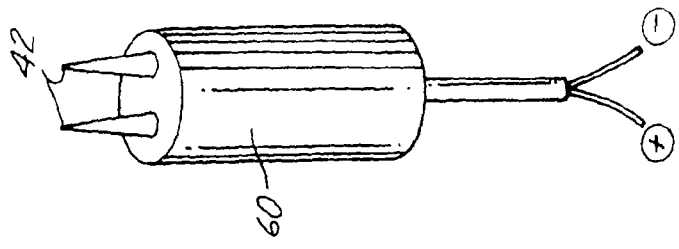
FIG. 3a illustrates an applicator with two needle like electrodes.

In FIG. 3 different versions of applicators are schematically shown. FIG. 3a illustrates an applicator 60 with two needle-like electrodes 64. FIG. 3b shows an applicator 64 with an array of needle-like electrodes 64. FIG. 3c depicts an applicator 66 like that shown in FIG. 2 and comprising a needle-like electrode 42 and a flat electrode such as electrode 44.

Figure 4B:
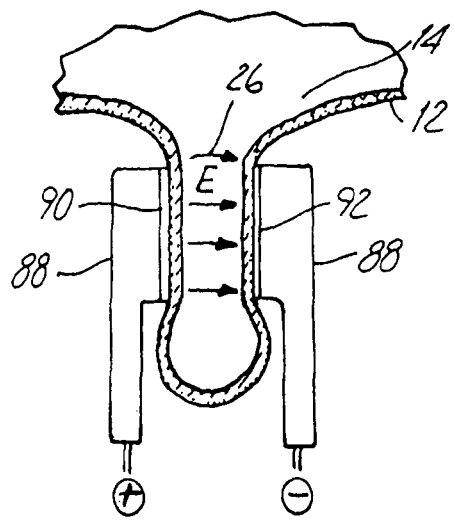
FIG. 4b is a schematic illustration of the forceps flat electrodes in closed position shown during electroporation treatment.
Figure 4A:
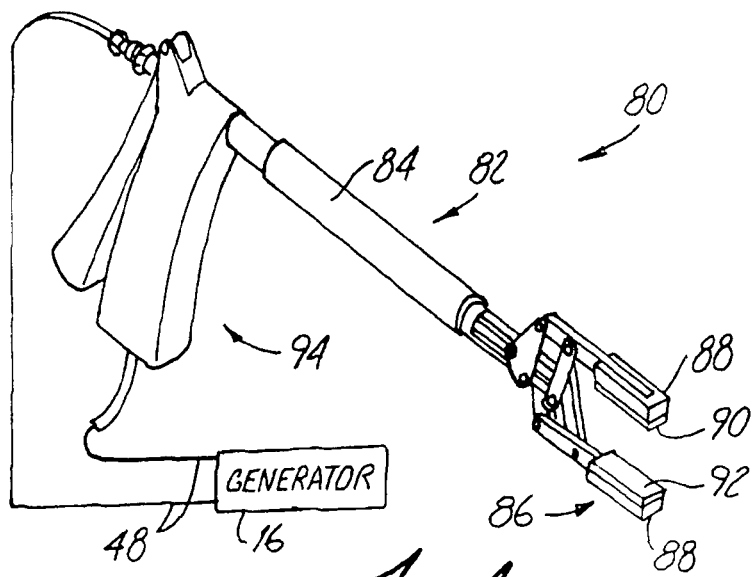
FIG. 4a is a perspective view of a forceps type applicator with two flat electrodes in an open position.

FIGS. 4a and 4b illustrate another embodiment 80 of an electroporation system in accord with the present invention useful for bulk fat reduction. System 80 includes an applicator 82 comprising a body or support member 84 supporting calipers or forceps apparatus 86. The calipers apparatus 86 includes a pair of pivotable arms 88 mounted at the distal end thereof. The arms 88 support a pair of electrodes 90 and 92. Applicator 82 may include a pistol grip 94 mounted on a proximal end of the elongated tubular support member 84 for enabling ease of manipulation of same. The electrodes 90 and 92 are mounted on a moveable linkage so that the electrodes are moveable toward and away from each other. A power supply 16 and electrical connectors 48 are also included within a system 80 to provide pulse electrical power to the electrodes 90 and 92.

FIG. 4b schematically illustrates an electroporation treatment utilizing system 80. As shown in the figure, a "fold" of skin 12 with underlying subcutaneous tissue—fat—14 is compressed between arms 88 and thus electrodes 90 and 92. A uniform electric field 26 is applied to the skin 12 and subcutaneous tissue 14 clamped between electrodes. Only the large fat cells are killed in this field configuration because the cells of the dermis are spared death because of their small size.

Figure 5:
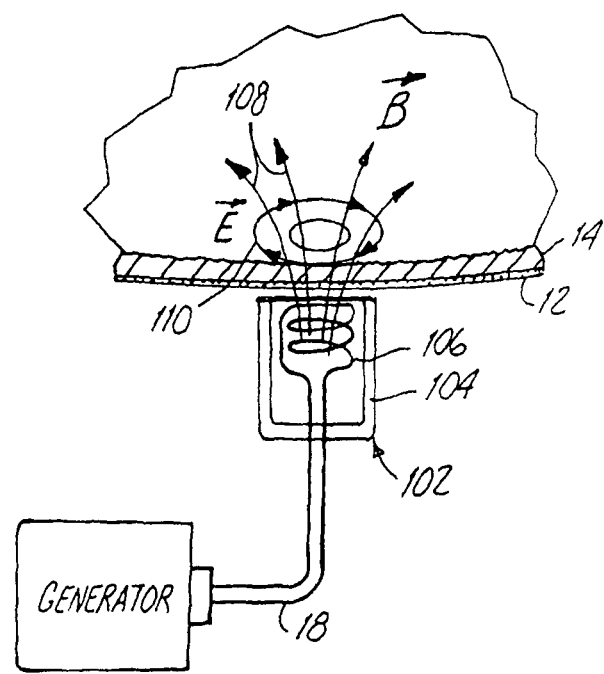
FIG. 5 is a schematic illustration of an apparatus for electroporation treatment for weight loss with electrodeless applicator.

FIG. 5 schematically illustrates another embodiment of the present invention including an electrodeless system 100. System 100 includes a high pulse current power supply 16 and an appropriate electrical connector 18 extending to an applicator 102. Applicator 102 comprises a housing 104 and an electromagnetic coil 106 disposed therein. Coil 106 generates a magnetic field 108 that is applied to the skin 12 and the subcutaneous tissues 14. The pulsed magnetic field 108 in the tissue exists only about 10 microseconds. The energy of rapidly changing magnetic field transforms into a curl electric field 110, which creates eddy currents in tissue and provides the electroporation treatment for killing the fat cells in the tissue 14. Preferably, the curl electric field generated in the subcutaneous tissue is in the range of 30 to 50 Volt/mm, and the duration of the pulses is 5 to 20 microseconds.

Figure 6:
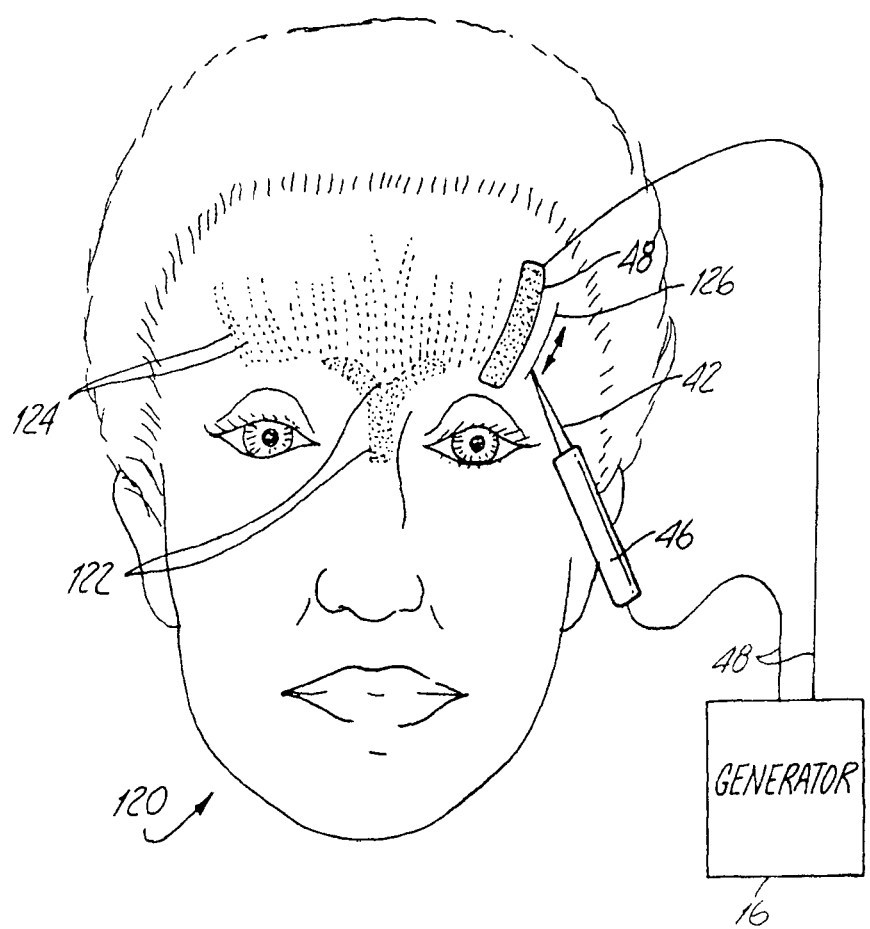
FIG. 6 is a frontal view of a human head with schematically shown electroporation treatment for removal of the forehead wrinkles and glabellar frown lines.

FIG. 6 schematically illustrates a frontal view of human head 120 with glabellar frown lines 122 and forehead wrinkles 124. An embodiment of the present invention Such as system 40 is shown in application. Electrode 44 is shown applied to the forehead and the needle electrode 42 is moved over the skin where treatment is desired. Moving the electrode tip along the skin creates a line of necrotic subcutaneous fat cells, which later are metabolized by the body. An exemplary line of treatment 126 is shown in the Figure. Multiple applications of the electrode along predetermined lines on the face or neck create shrinkage of the skin and the subcutaneous fat volume underlying the treated area.

Figure 7:
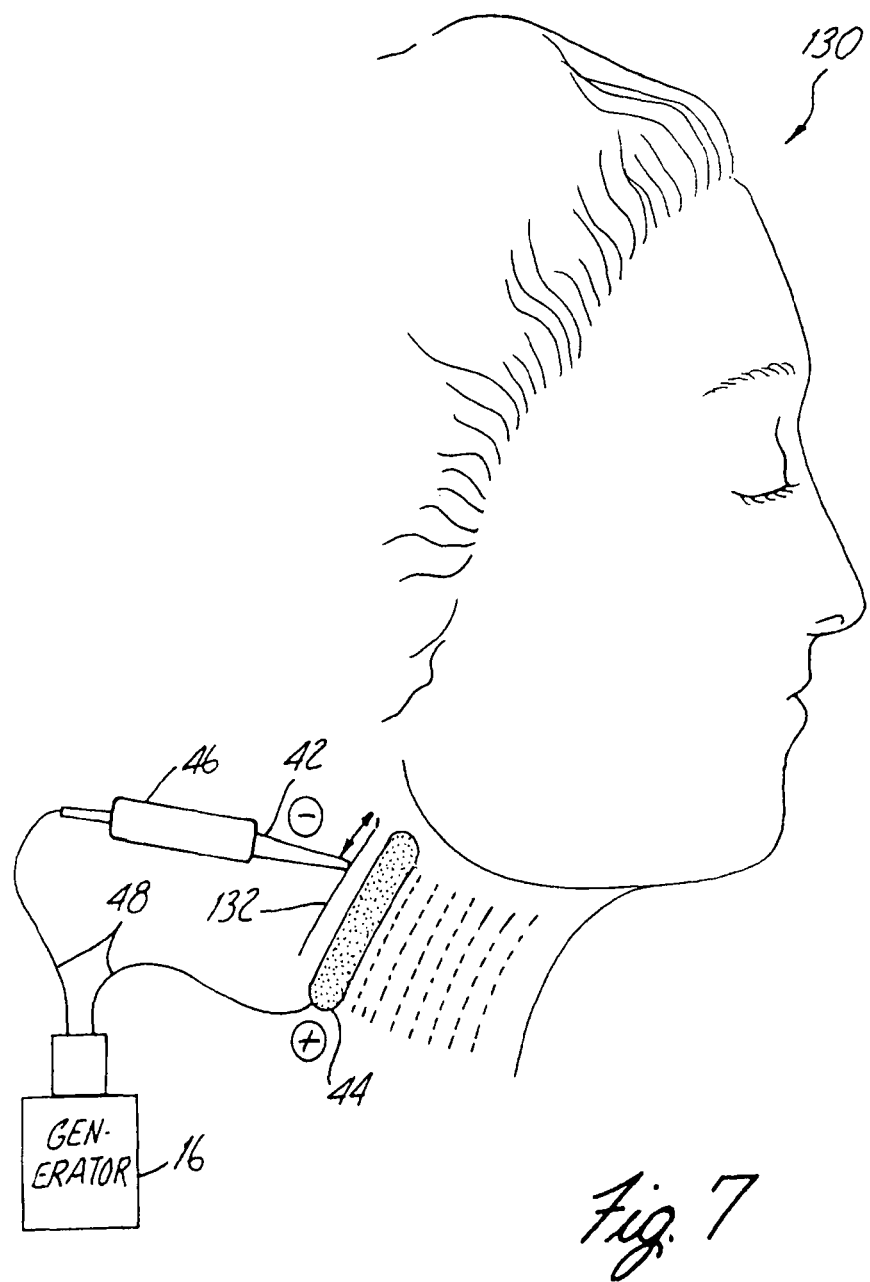
FIG. 7 is a lateral view of a human head with schematically shown electroporation treatment for a neck lift.

FIG. 7 depicts a lateral view of a human head 130 during a neck lift electroporation procedure using an electroporation system in accord with the present invention such as system 40. The figure illustrates an exemplary line of electroporation treatment 132.

The present invention having thus been described, other modifications, alterations, or substitutions may now suggest themselves to those skilled in the art, all of which are within the spirit and scope of the present invention. It is therefore intended that the present invention be limited only by the scope of the attached claims below.

What is claimed is:

1. A method for sculpting a human body comprising:
   providing:
      an applicator comprising first and second electrodes defining a treatment area therebetween, the treatment area adapted to accept a portion of the human body comprising at least one of skin, subcutaneous tissue, and fat, and
      a generator operably connected to the applicator;
   engaging the applicator with a surface of skin on the human body, wherein the first and second electrodes remain outside of the human body;
   retaining the portion of the human body within the treatment area; and
   applying a plurality of electrical pulses between the first and second electrodes in an amount sufficient to irreversibly open pores in fat cells in the retained portion of the human body.

2. The method of claim 1, wherein the portion of the human body comprises all of skin, subcutaneous tissue and fat.

3. The method of claim 1, wherein the first and second electrodes are positioned on opposing sides of the treatment area.

4. Repeating the method of claim 1 on a plurality of different portions of the human body according to a pre-determined treatment plan.

5. The method of claim 1, wherein the step of applying further comprises applying electrical pulses whose amplitude is in a range of 20 Volt/mm and 2000 Volt/mm.

6. The method according to claim 1, wherein the step of applying a plurality of electrical pulses further comprises applying electrical pulses whose amplitude is above 20 Volt/mm.

7. The method of claim 1, wherein the step of applying a plurality of electrical pulses further comprises applying electrical pulses whose duration is in a range of 10 microseconds and 100 milliseconds.

8. The method of claim 1, wherein the step of applying a plurality of electrical pulses further comprises applying electrical pulses whose amplitude is in a range of 20 Volt/mm and 2000 Volt/mm and whose duration is in a range of 10 microseconds and 100 milliseconds.

9. A method for a skin tightening and fat reduction treatment comprising:
   providing:
      an applicator comprising first and second electrodes defining a treatment area therebetween, the treatment area adapted to accept a portion of the human body comprising at least one of skin, subcutaneous tissue, and fat, and
      a generator operably connected to the applicator;
   engaging the applicator with a surface of skin on the human body;
   retaining the portion of the human body within the treatment area;
   applying a first plurality of electrical pulses between the first and second electrodes in an amount sufficient to irreversibly open pores in fat cells of the portion of the human body; and
   applying a second plurality of electrical pulses between the first and second electrodes in an amount sufficient to irreversibly open pores in skin cells of the portion of the human body.

10. Repeating the method of claim 9 on a plurality of different portions of the human body according to a pre-determined treatment plan.

* * * * *